United States Patent [19]

Gordon et al.

[11] Patent Number: 4,604,964
[45] Date of Patent: Aug. 12, 1986

[54] TISSUE PROCESSING APPARATUS

[75] Inventors: Alan J. Gordon, Liverpool; David W. Sterritt, Warrington; Robert Evans, Liverpool, all of England

[73] Assignee: Shandon Southern Products Limited, Runcorn, England

[21] Appl. No.: 701,818

[22] Filed: Feb. 19, 1985

Related U.S. Application Data

[63] Continuation of Ser. No. 426,913, Sep. 29, 1982, abandoned.

[30] Foreign Application Priority Data

Oct. 20, 1981 [GB] United Kingdom ............... 8131663

[51] Int. Cl.⁴ .................................................. B05C 3/02
[52] U.S. Cl. ...................................... 118/50; 118/421; 118/429; 118/696
[58] Field of Search ............... 118/50, 421, 429, 696, 118/697, 698, 699, 704

[56] References Cited

U.S. PATENT DOCUMENTS

| | | | |
|---|---|---|---|
| 3,348,774 | 10/1967 | Wiggins | 118/704 X |
| 3,892,197 | 7/1975 | Kinney et al. | 118/429 X |
| 4,054,692 | 10/1977 | Monmarson | 118/50 X |

Primary Examiner—John P. McIntosh
Attorney, Agent, or Firm—Vaden, Eickenroht, Thompson & Boulware

[57] ABSTRACT

A tissue processing apparatus comprises a processing chamber (1), a plurality of reagent containers (5), only one of which is illustrated, and a selector valve (2) for sequentially connecting the processing chamber (1) to each of the said reagent containers (5) to transfer fluid between the chamber and such a container. A vacuum/compression pump (6) and a changeover valve system connected to each of the reagent containers (5) and to the processing chamber (1) is operable to promote reagent flow in a required direction between a reagent container (5) and a processing chamber (1) while maintaining a closed circuit for reagent and gas displaced by the pump between the chamber and the container.

18 Claims, 6 Drawing Figures

4,604,964

TISSUE PROCESSING APPARATUS

This is a continuation of application Ser. No. 426,913, filed Sept. 29, 1982, now abandoned.

BACKGROUND OF THE INVENTION

This invention relates to tissue processing apparatus for the processing of histological and like tissue specimens by sequential treatment with a series of reagents. More particularly the invention relates to tissue processing apparatus of the kind comprising a single processing chamber for the reception of one or more tissue specimens and to which reagents are supplied, in turn, for the sequential treatment of the tissue specimen(s) therein with such reagents. Typically in the preparation of tissue specimens for microscopic examination, the specimens are subjected progressively to fixation, dehydration, clearing, staining and embedding in a suitable wax to facilitate sectioning of the tissue specimens. The dehydration stage usually involves the treatment of a batch of specimens with alcohol reagents of progressively increasing concentration, and the clearing stage involves the treatment of these dehydrated specimens one or more times with a clearing agent such as xylene to displace the alcohol. The dehydration and clearing stages as well as preceding fixations and/or subsequent staining and/or wax embedding stage may all be accomplished in the single processing chamber of apparatus of the kind with which the invention is concerned, by feeding the relevant processing fluids to that chamber, in turn, from individual sources.

Known single-chamber apparatus of this kind, for instance apparatus such as disclosed in U.S. Pat. Nos. 2,959,151, 3,227,130 and 4,141,312, utilises a variety of arrangements for feeding the various fluids to the processing chamber and for removing those fluids from the chamber following a treatment phase with such a fluid. However none of these arrangements makes significant provision fully to prevent the escape into the environment of leakages of the processing fluids and of their vapours, for instance in the air displaced from the processing chamber on admission of fluid thereto and in the air displaced from containers for the processing fluids during transfer of such fluids to and from the processing chamber. As many of the processing fluids are volatile their vapours are contained in significant amounts in the air displaced from the processing chamber and the fluid containers.

Moreover, the fluids become contaminated with materials eluted from the tissue specimens treated by the fluids and such materials (which may be highly toxic) may appear in the said displaced air and escape capture by any means that may be provided, such as activated carbon filters in air vent lines, for limiting the discharge of the processing fluid vapours.

The aim of the present invention is to avoid or mitigate this problem.

SUMMARY OF THE INVENTION

The invention provides, in tissue processing apparatus comprising a processing chamber, a plurality of reagent containers and a selector valve for sequentially connecting the processing chamber to each of said reagent containers to transfer fluid between the chamber and such a container, the improvement that comprises a vacuum and compression pump means and changeover valve system connected to each of said reagent containers and to the processing chamber and operable to promote reagent flow in a required direction between a reagent container and the processing chamber while maintaining a closed circuit for reagent and gas displaced by the pump means between the chamber and the container.

The changeover valves may comprise electrically-operated valves that can be switched to reverse the pump connections to the processing chamber and reagent containers to facilitate the supply of reagent to the processing chamber and removal of the reagent therefrom after completion of a treatment phase.

Preferably an isolating valve is included in the fluid transfer connection from the selector valve to the processing chamber to prevent leakage of reagent from the processing chamber during a treatment phase.

An accumulator may be connected to said closed circuit to accommodate volumetric changes in the circuit contents, such as may occur if a leak develops or if the ambient temperature alters, the provision of this accumulator minimises venting of gas to the environment. The accumulator may be a compliant bag.

Pressure relief valve means for relieving excess pressure in the closed circuit may also be included, to ensure that any leakage that may occur, for instance at the selector valve, does not adversely affect the operation of the apparatus.

The pressure relief valve preferably relieves both under-pressure and over-pressure in the closed circuit. Such pressure relief valve means may be constituted by a pair of pressure relief valves, one connected to relieve over-pressure and the other connected to relieve under-pressure.

A filter is desirably associated with the or each said relief valve means to prevent the venting of toxic and/or inflammable vapours from the closed circuit if an over-pressure in said circuit occurs, and to ensure that no contaminants enter the closed circuit in the event of air being taken into the circuit to relieve an under-pressure.

Certain embodiments of the invention are described by way of example and illustrated in the accompanying drawings.

DESCRIPTION OF EMBODIMENTS

Figure 1:
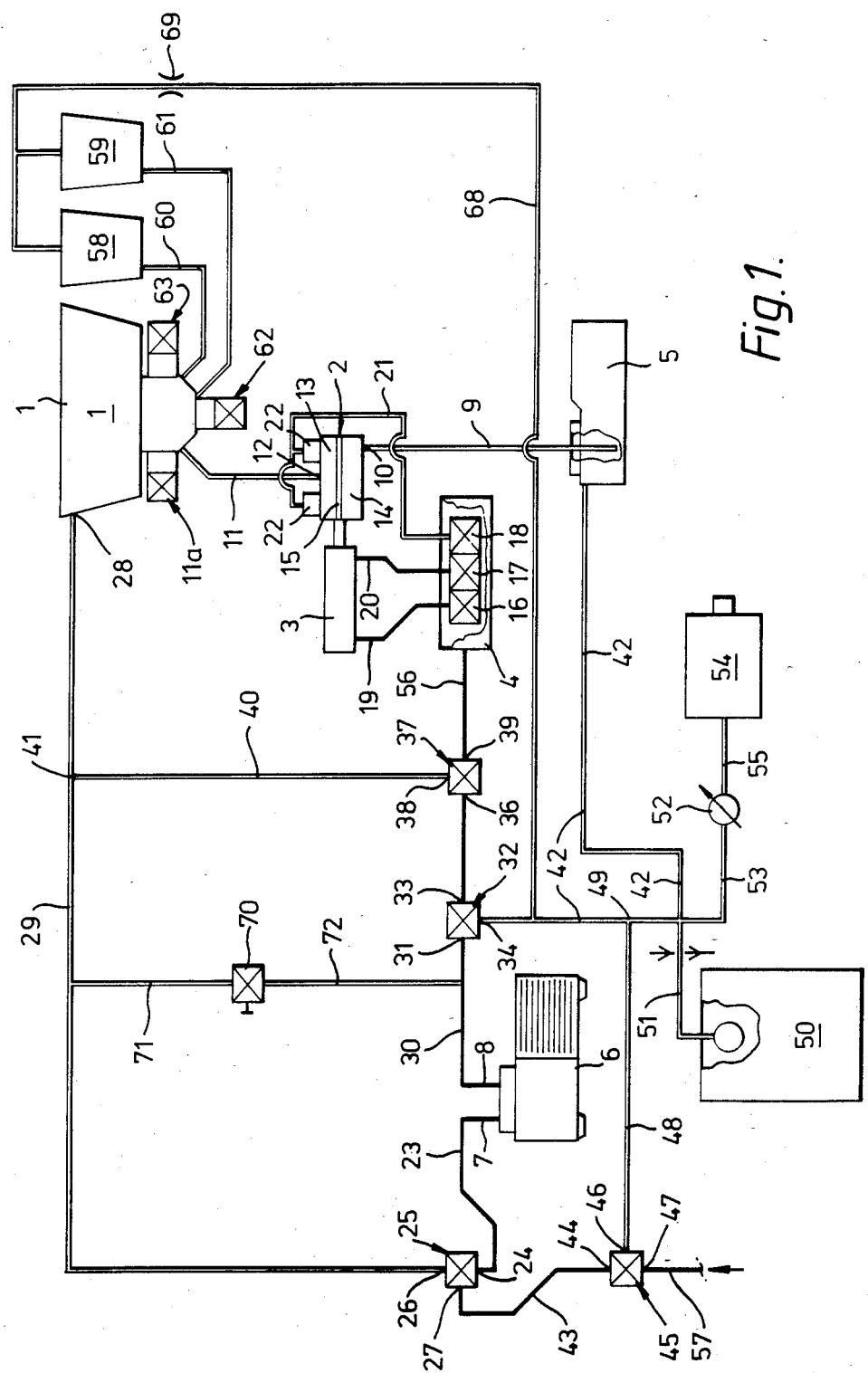
FIG. 1 is a schematic illustration of a single chamber tissue processing apparatus in accordance with the invention and illustrates the apparatus set in an "indexing" mode.

The single chamber processing apparatus shown in FIG. 1 comprises a processing chamber 1, a selector valve 2 having actuator means 3 and a sensing/control unit 4 associated therewith, a plurality of reagent containers 5 (only one of which is illustrated for clarity), and a vacuum/compression pump 6 having a suction port 7 and a pressure port 8.

An individual conduit 9 connects each of said reagent containers 5 to a respective selectable port 10 of the selector valve 2 and a conduit 11 connects the processing chamber 1 to a common port 12 of the selector valve 2. The selector valve 2 is operable to connect its common port 12 to any one of the ports 10 for transfer of fluid between the chamber 1 and any selected one of the containers 5. A valve 11a positioned at the junction of the conduit 11 with the processing chamber 1 enables of the processing chamber 1 to be isolated from the valve 2, e.g. during a treatment phase of a batch of tissue specimens. The selector valve 2 may be of any suitable construction but preferably is a rotary selector valve. Thus the valve 2 conveniently has an upper rotatable member 13 and a lower fixed member 14 so arranged that a valve joint interface 15 is formed between them, the rotatable member 13 having a single pathway (not shown) that extends from the central common port 12 to an eccentric position at the valve joint interface 15 and the fixed member 14 having a plurality of pathways each of which extends from a selectable port 10 to the valve joint interface. The member 13 is arranged to be indexed through a series of positions in each of which a continuous pathway is formed between the common port 12 and an individual one of the selectable ports 10. To restrain leakage at the valve joint interface 15 a venturi restriction is provided in the pathway at this point.

The actuator means 3 serves to operate the selector valve 2 to connect its common port 12 to a selected one of the selectable ports 10, and in the case of the preferred rotary selector valve is arranged to index the rotatable member 13 of the selector valve. Preferably the actuator means 3 is a pneumatically-operated piston and cylinder assembly coacting with indexing pins (not shown) on the rotatable member 13 and powered by compressed air from the vacuum/compression pump 6.

Operation of the actuator means 3 is controlled by the sensing/control unit 4 which comprises three valves 16, 17, 18, valve 16 being joined by a conduit 19 to the actuator means 3 for providing a forward stroke piston, valve 17 being connected by a conduit 20 to the actuator means 3 for providing a reverse stroke of the piston and valve 18 being connected by a conduit 21 to pneumatic sensor units 22 that cooperate with the rotatable member 13 of the selector valve 2 to sense and signal the position of the latter.

As will be further described below, the sensing/control unit 4 may be connected to the pressure port 8 of the vacuum/compression pump 6 for the supply of compressed air to the unit 4.

The suction port 7 of the pump 6 is connected by a conduit 23 to the common port 24 of a changeover valve 25 that has selectable ports 26,27, the port 26 being connected to a port 28 of the processing chamber 1 by a conduit 29.

The pressure port 8 of the pump 6 is connected by a conduit 30 to the common port 31 of a changeover valve 32 that has selectable ports 33, 34. The port 33 of the valve 32 is connected by a conduit 35 to the common port 36 of a further changeover valve 37 that has selectable ports 38, 39, the port 38 being connected via a conduit 40 to a junction point 41 in the conduit 29. A conduit 42 connects the port 34 of the valve 32 to each of the reagent containers 5.

The port 27 of the valve 25 is connected by conduit 43 to the common port 44 of another changeover valve 45 having selectable ports 46, 47, the port 46 being connected by a further conduit 48 to a junction point 49 in the conduit 42.

The changeover valves 25, 32, 37 and 45 are electrically operated and as will be described can be set so as to connect either the suction port 7 or the pressure port 8 of the pump 6 to the processing chamber 1, and the other port of the pump to the reagent containers 5, in a closed circuit so that operation of the pump 6 enables transfer of reagent, in either direction as desired, between the processing chamber and a reagent container selected by means of the valve 2. Transfer of reagent in this manner, i.e. in a closed circuit system, substantially reduces the problem of venting toxic and/or inflammable vapours into the environment.

A compliant air bag 50 is connected to the conduit 42 by a conduit 51, to serve as an accumulator to accommodate variations in the volume of gas in the closed circuit, such as may occur if a leak develops in the system, and to accommodate associated pressure changes a pressure relief valve 52 is connected to the conduit 42 by a conduit 53. A filter 54 on the outlet 55 of the pressure relief valve 52 prevents the venting of any toxic and/or inflammable vapours into the environment. As any leak may be either inwards or outwards, the pressure relief valve 52 is adapted to relieve both overpressure and underpressure in the system. In the embodiment described the pressure relief valve 52 is adapted to open at a pressure of up to $\pm 2$ p.s.i. ($\pm 14$ kPa)(gauge), the system being designed to operate with a gauge pressure within the range $\pm 1$ p.s.i. ($\pm 7$ kPa).

Figure 5:
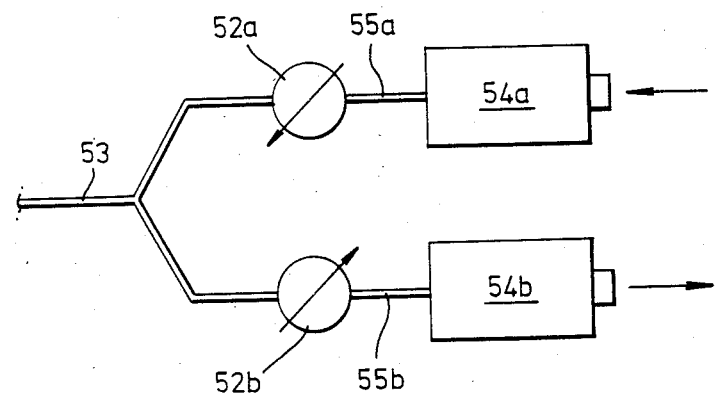
FIG. 5 shows schematically a preferred form of a part of the apparatus of FIG. 1.

As is illustrated schematically in FIG. 5, the pressure relief valve 52 is conveniently constructed as a pair of pressure relief valves 52a and 52b, the valve 52a being adapted to relieve under-pressure and a suitable filter 54a, for example a mesh filter, being connected to the inlet 55a of the valve 52a to prevent the intake of contaminants. The valve 52b is adapted to relieve overpressure and a suitable filter 54b, for example an activated charcoal filter, is connected to the outlet 55b of the valve to prevent the venting of toxic and/or inflammable vapours into the environment.

Referring again to FIG. 1 the sensing/control unit 4 is connected to the port 39 of the valve 37 by a conduit 56 for the supply of compressed air to the actuator means 3 and to the pneumatic sensor units 22. An inlet conduit 57, connected to the port 47 of the valve 45, is provided to enable the supply of fresh air to the vacuum/compression pump 6, when the latter is to deliver compressed air to the actuator means 3 and the sensor units 22, both of which vent spent air to atmosphere.

A pair of wax containers 58, 59 are connected to the processing chamber 1 by conduits 60, 61 via valves 62, 63. The containers 58, 59 and their associated conduits and valves are suitably insulated and provided with heating means to maintain the wax in a fluid state. The supply of wax to the processing chamber 1 may be by gravity feed from these containers, flow being assisted by a vacuum applied to the processing chamber 1 by the pump 6 or, as shown in FIGS. 1 to 4, sealed containers 58, 59 may be connected by a suitable conduit 68 to the pump 6 so as to be incorporated in the closed circuit of the processing apparatus. A restrictor 69 may be provided in conduit 68 to direct the gas flow preferentially through conduit 42 to the reagent containers 5 when reagent flow between the processing chamber 1 and the reagent containers is required, by restricting flow to the wax containers 58, 59.

Figure 6:
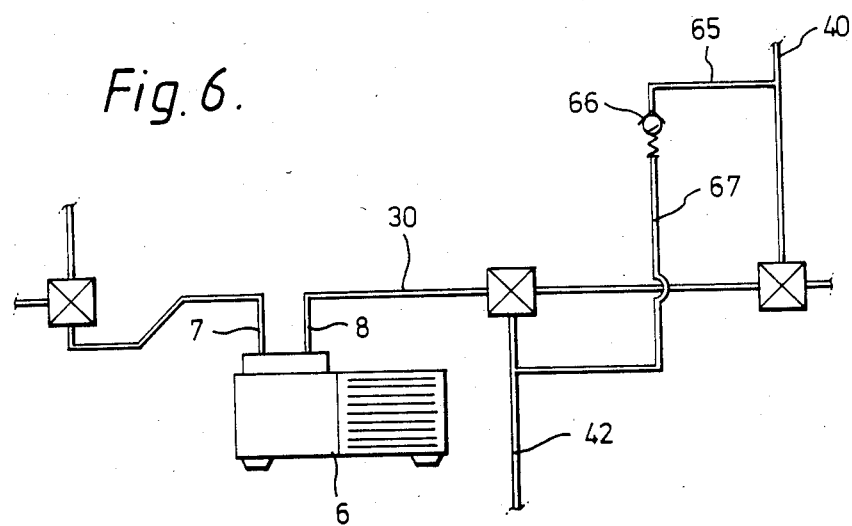
FIG. 6 shows an alternative arrangement of a part of the apparatus of FIG. 1.

It is desirable that the pressure applied to the processing chamber 1 be maintained within a specified upper limit, to facilitate safe operation of the apparatus, whilst avoiding excessive venting of the apparatus to the atmosphere. FIG. 6 illustrates a modification to the apparatus shown in FIG. 1 which provides for control of the processing chamber pressure. As shown in FIG. 6, the inlet 65 of a unidirectional pressure relief valve 66 is joined to the conduit 40 and the outlet 67 of the valve 66 is connected to the conduit 42, the arrangement providing a pathway between the pressure and suction ports of the pump 6. A rise in pressure above a value set by the sensitivity of the relief valve 66 will open the valve and cause a shunting of excess air around the pump.

Preferably, a further valve 70 is provided to enable relief of the vacuum from the processing chamber 1 (as will be discussed below). The valve 70 could suitably be of the same design as the changeover valves described above, having an inlet 71 connected with the conduit 29, one outlet 72 being connected with the conduit 30 and the other being blanked off, to provide a "no-flow" position.

In the illustrated embodiment all of the changeover valves shown are operable automatically by a central processor control means (not shown).

Referring to FIGS. 1 to 4, a single operating cycle for this apparatus comprises:

(1) Indexing of the member 13 of the selector valve 2 for connection of a desired reagent container with the processing chamber;

(2) Sensing of the relative position of the valve member 13 to confirm correct positioning for the desired reagent container connection;

(3) Transfer to the processing chamber of the desired reagent from its container; and (4) Return of the reagent from the processing chamber to its container after a desired period.

FIG. 1 shows the circuit connections for indexing of the selector valve 2 by operation of the pump 6, the valves 32 and 37 being set so as to connect the sensing-/control unit 4 to the pressure port 8 of the pump 6 via conduits 30, 35 and 56, and the valves 25, 45 being set so as to connect the suction port 7 of the pump 6 to the inlet conduit 57, enabling the pump to draw in and supply fresh air to the sensing/control unit 4. To effect indexing, the valve 16 of the sensing/control unit 4 is opened to allow compressed air to pass along the conduit 19 to the actuator means 4 to effect a forward stroke of its piston (not shown) which engages an indexing pin (not shown) on the rotatable member 13 of the selector valve 2 to rotate the selector valve 2 by one step, whereafter closure of the valve 16 and opening of the valve 17 effects the return stroke of the piston, which return stroke preferably serves to more accurately position the member 13 of the selector valve 2, by means of a ratchet mechanism (not shown).

Figure 2:
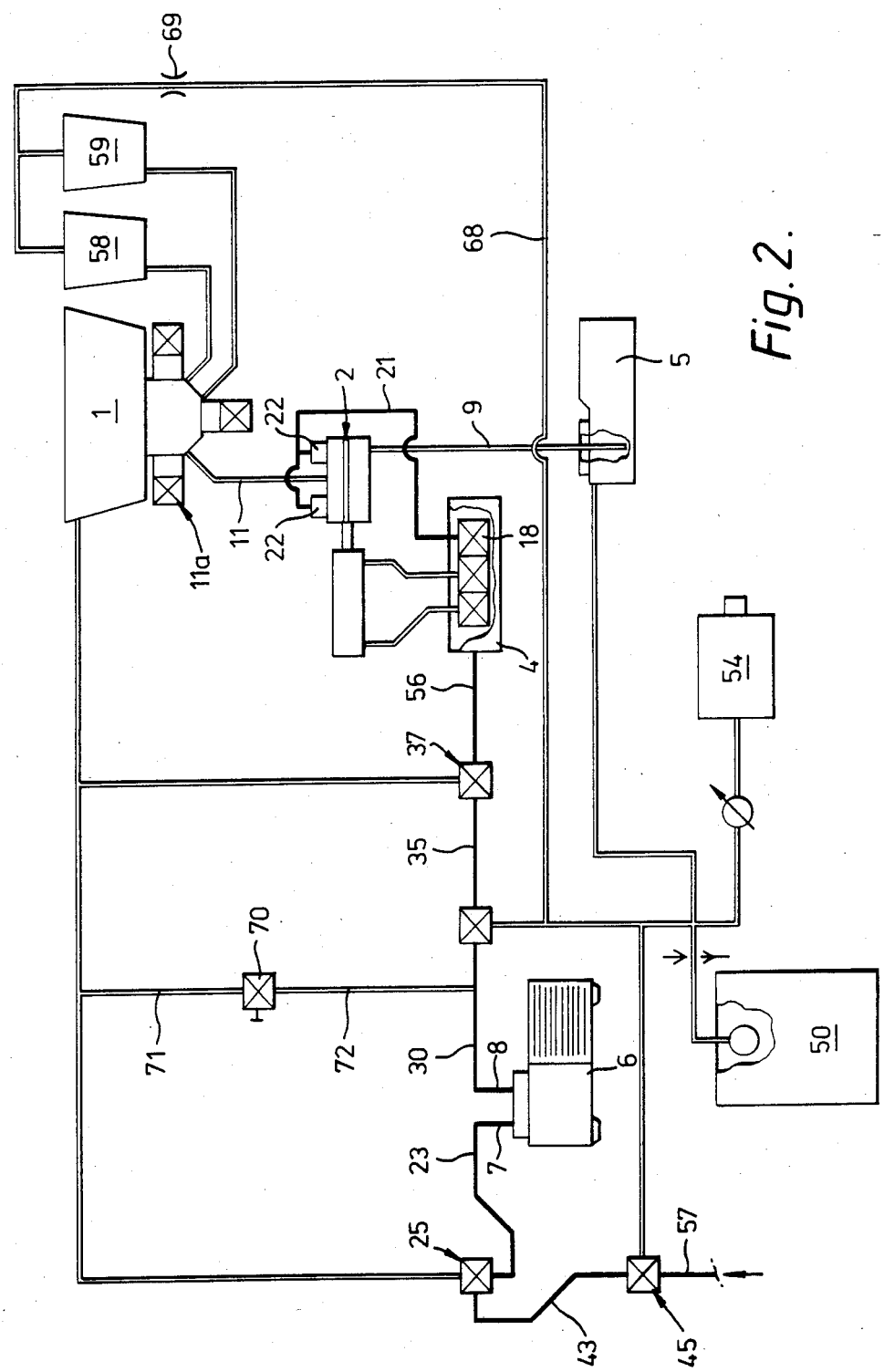
FIG. 2 shows the apparatus of FIG. 1 set in a "sensing" mode.

FIG. 2 shows the circuit connections for sensing the position of the selector valve 2 following an indexing operation, (which may consist of one or a plurality of forward and return strokes of the piston of the actuator means 3) to check that the valve is properly positioned for connecting a selected one of the conduits 9 with the conduit 11. In this mode, air is directed to the sensing-/control unit 4, as in the indexing operation described above, but both valves 16 and 17 are closed while valve 18 is opened to allow flow through conduit 21 to the pneumatic sensing units 22. Preferably the output of the units 22 is interpreted and displayed, as well as being sent to the central processor control means for control of the indexing operation.

Figure 3:
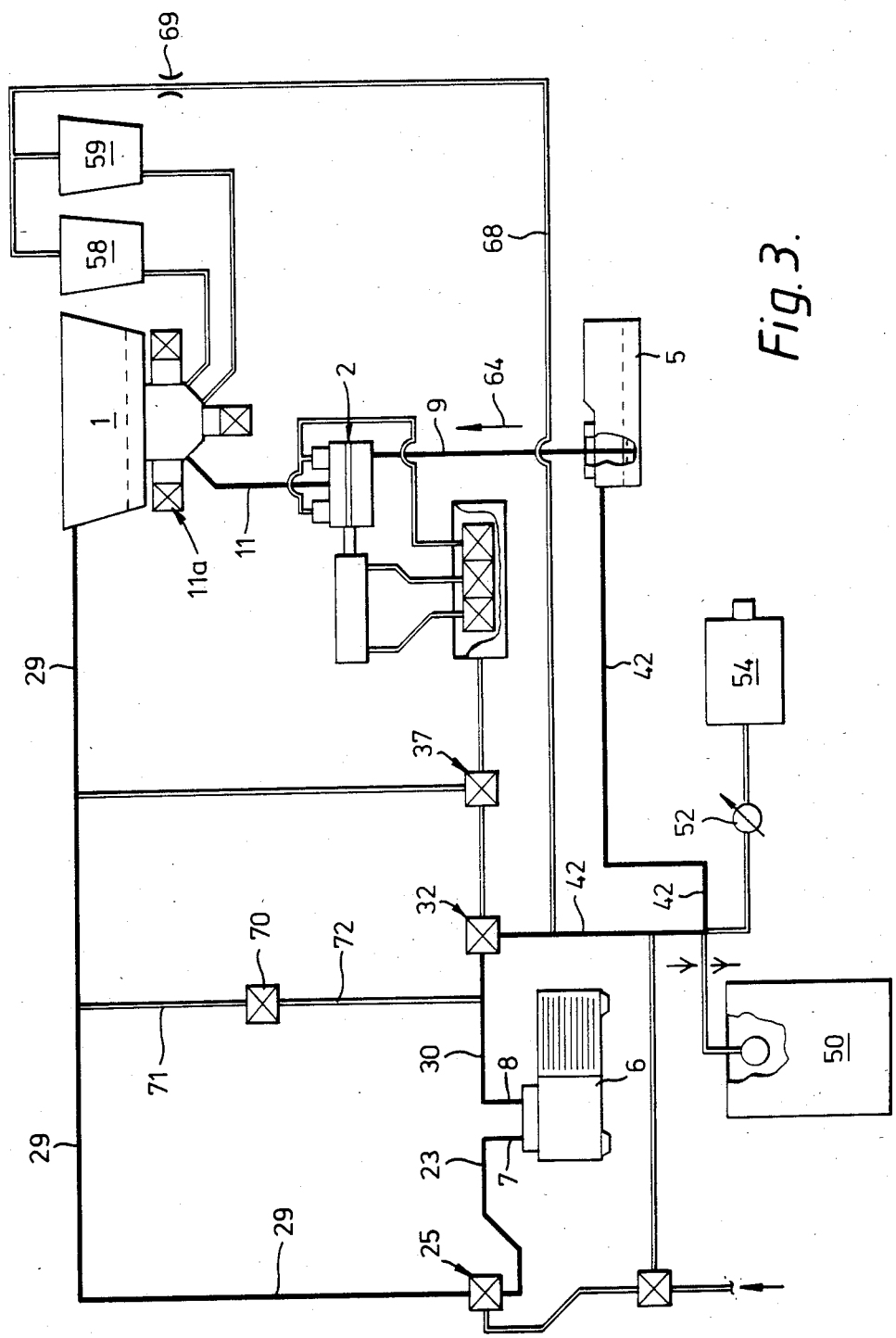
FIG. 3 shows the apparatus of FIG. 1 set in a "vacuum" mode for the supply of a reagent to the processing chamber.

FIG. 3 shows the circuit connections for transfer of a reagent from a reagent container 5 to the processing chamber 1 for treatment of a batch of specimens therein. The valve 25 is switched to connect the conduit 23 to the conduit 29 and thus to connect the suction port 7 of the pump 6 to the processing chamber 1, while the valve 32 is switched to direct flow from conduit 30 to conduit 42 and thus to connect the reagent container 5 to the pressure port 8 of the pump 6. The valve 70 is switched to its "no-flow" position so that no air passes through it. By operation of the pump 6, the combination of the vacuum applied to the processing chamber 1 and of the pressure applied to the reagent container 5 causes the reagent to flow from the reagent container 5 through the conduit 9, the selector valve 2 and the conduit 11, to the processing chamber 1 in a direction indicated by the arrow 64, air displaced from the chamber 1 being transferred to the container 5 to replace the reagent displaced therefrom. Preferably, any partial vacuum remaining in the processing chamber 1 after completion of the transfer operation is relieved by connecting the conduit 29 with the conduit 30 via the valve 70.

A sensor (not shown) senses the pressure difference between the suction port 7 and the pressure port 8. When reagent is present in the conduits 9, 11, a pressure difference of up to 10 p.s.i. (70 kPa) is sensed. The precise value of the pressure difference is dependent upon the relative positions of the liquid containers and is therefore variable. However when all of the reagent has passed into the processing chamber 1, this pressure difference drops towards zero owing to the closed circuit existing between the pump 6, the processing chamber 1 and the reagent container 5. The sensing of the drop in pressure difference is used to signal the central processor to switch off the pump and to close the valve 11a for the duration of the treatment period utilising that reagent. If vacuum conditions are required in the processing chamber for the treatment period valve 70 is set to the "no-flow" position and the pump is operated until the required level of vacuum is reached. If no vacuum is required valve 70 should be set to connect the conduits 29 and 30, to provide a pathway between the processing chamber 1 and the air bag 50.

Figure 4:
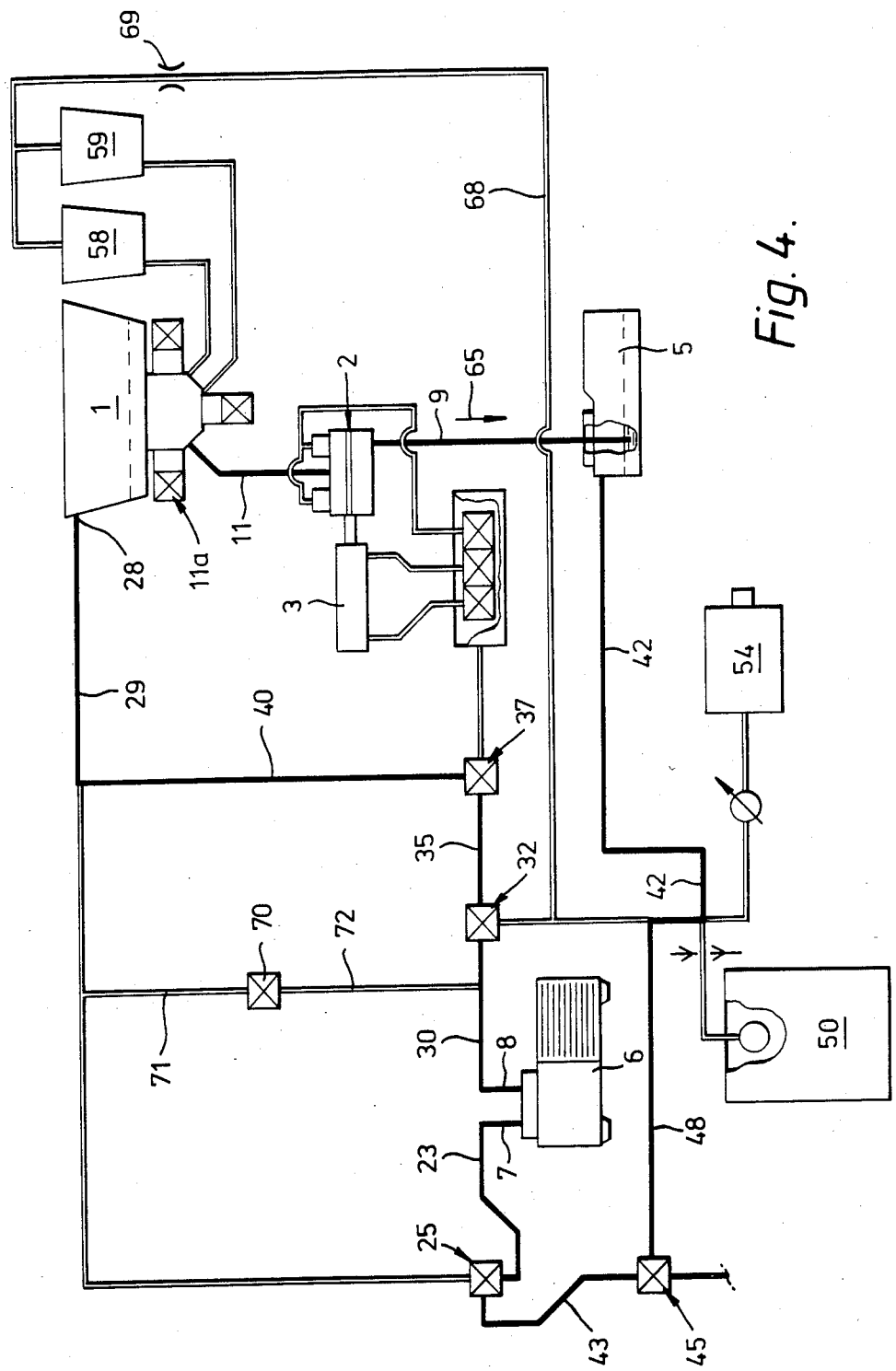
FIG. 4 shows the apparatus of FIG. 1 set in a "compression" mode for the removal of a reagent from the processing chamber.

The return of reagent from the processing chamber 1 to its container 5 is accomplished by operating the pump 6 with its suction port 7 connected to the reagent container 5 and its pressure port 8 connected to the processing chamber 1 with the valve 11a open. FIG. 4 shows the circuit connections for this transfer, the valves 32 and 37 being set to direct flow from the pressure port 8 via conduits 30, 35, 40 and 29 to the processing chamber 1, and valves 25 and 45 being set to direct flow along conduits 43, 48 and 42 and thus to connect the suction port 7 of the pump 6 to the reagent containers 5. Operation of the pump 7 now leads to the application of a vacuum to the reagent containers 5 and of pressure to the processing chamber 1, causing the reagent to flow from the processing chamber 1, through the conduit 11, the selector valve 2, and the conduit 9 back into its reagent container 5, this flow being in a direction indicated by the arrow 65. As in the previous transfer of reagent to the processing chamber 1, the return of all reagent to its container is sensed by a drop in pressure differential across the pump 6, and this causes the central processor control means to switch off the pump and reclose the valve 11a.

This cycle is repeated for each reagent that is required to be supplied to the processing chamber 1. As shown in the Figures, wax can be transferred to the chamber 1 from the wax sources 58, 59 as and when required.

Using a suitable central processor control, a variety of treatment programs can be selected and carried through without further operator intervention and without need for any special precautions to be taken, when a selected program involves the use of, e.g. a noxious or otherwise dangerous reagent, because the escape of any reagent or effluent into the environment is precluded by the use of a closed circuit for both fluids and gases during all fluid transfers. If, as is preferred, the apparatus incorporates a selector valve and the absolute and differential pressures at the selector valve are so arranged that any leakage at this valve is into the system, most leakage flows can be accommodated by the compliant bag. When the compliant bag is full any further leakage would cause the development of an over-pressure, which will be vented by the pressure relief valve 52. To minimise the need for such venting, the contents of the bag may be discharged from time to time—e.g. by replacing the bag and disposal of the filled bag. In order to avoid liquid collecting in the bag a vapour trap (not shown) may be provided. Preferably, the vapour trap is self draining.

Although for convenience of illustration the changeover valves 24, 32, 37, 45, and 70 are shown separated in space and connected to the pump 6 and to one another by conduits, in practical constructions all these valves are disposed closely adjacent to one another, e.g. by mounting on a manifold block on the pump 6 so as to facilitate their interconnection and, especially, to minimise the contained volume of that part of the closed circuit (including the pump 6) that is utilised with the latter to supply compressed fresh air to the sensing/control unit 4, whereby any contamination of such compressed air by mixing with residual circuit air in the common part of the closed circuit is minimised.

What is claimed is:

1. A tissue processing apparatus, comprising:
   a processing chamber for processing a tissue specimen;
   a plurality of reagent containers;
   a selector valve interconnected with said reagent containers and with said processing chamber for creating a fluid conduit between a selected reagent container and said processing chamber;
   a pump having a suction port and a pressure port and adaptable to provide both a vacuum and a compressed gas; and
   changeover valve means interconnected with said pump, with said processing chamber and with said reagent containers, said changeover valve means having first and second selectable operative conditions, said first selectable operative condition connecting said suction port of said pump with said processing chamber and said pressure port of said pump with said reagent containers, and said second selectable operative condition connecting said suction port of said pump with said reagent containers and said pressure port of said pump with said processing chamber, thereby in each said operative condition to establish a closed circuit comprising said pump, said processing chamber, said fluid conduit and said selected reagent container;
   whereby operation of said pump with said changeover valve means in said first operative condition enables transfer of reagent from said selected reagent container through said fluid conduit to said processing chamber, whereas operation of said pump with said changeover valve means in said second operative condition enables transfer of reagent from said processing chamber through said fluid conduit to said selected reagent container, and in each said operative condition without providing communication between the atmosphere external to said closed circuit and any one of said pump, said processing chamber or said reagent containers.

2. The tissue processing apparatus of claim 1 in which said changeover valve means is electrically-operated and is switchable between said selectable operative conditions.

3. The tissue processing apparatus of claim 1, further comprising:
   an isolation valve in a fluid transfer connection with said selector valve and said processing chamber.

4. The tissue processing apparatus of claim 1, further comprising:
   an accumulator connected to said closed circuit to accommodate volumetric changes in the circuit contents.

5. The tissue processing apparatus of claim 4, in which said accumulator comprises a compliant bag.

6. The tissue processing apparatus of claim 1, further comprising:
   a pressure relief valve means for relieving excess pressure in said closed circuit.

7. The tissue processing apparatus of claim 6, in which said pressure relief valve means relieves both under-pressure and over-pressure in said closed circuit.

8. The tissue processing apparatus of claim 7, in which said pressure relief valve means comprises a pair of pressure relief valves, one connected to relieve over-pressure and the other connected to relieve under-pressure.

9. The tissue processing apparatus of claim 6, further comprising:
   a filter associated with said pressure relief valve means to filter gas passing said valve means.

10. The tissue processing apparatus of claim 1, further comprising:
    pneumatically-powered means for operating said selector valve.

11. The tissue processing apparatus of claim 10, in which said pneumatically-powered means is actuated by air obtained from said pump.

12. The tissue processing apparatus of claim 11, further comprising:
    a valve controlling the connection of said pneumatically-powered means to said pump and isolating said pump from said closed circuit when said pump is connected to supply air to said pneumatically-powered means.

13. A tissue processing apparatus, comprising:
    a processing chamber for processing a tissue specimen;
    a plurality of reagent containers;
    a selector valve interconnected with said reagent containers and with said processing chamber for creating a fluid conduit between a selected reagent container and said processing chamber;

a pump having a suction port and a pressure port and adaptable to provide both a vacuum and a compressed gas;

changeover valve means interconnected with said pump, with said processing chamber and with said reagent containers, said changeover valve means having first and second selectable operative conditions, said first selectable operative condition connecting said suction port of said pump with said processing chamber and said pressure port of said pump with said reagent containers, and said second selectable operative condition connecting said suction port of said pump with said reagent containers and said pressure port of said pump with said processing chamber, thereby in each said operative condition to establish a closed circuit comprising said pump, said processing chamber, said fluid conduit and said selected reagent container;

an accumulator connected to said closed circuit to accommodate volumetric changes in the circuit contents;

whereby operation of said pump with said changeover valve means in said first operative condition enables transfer of reagent from said selected reagent container through said fluid conduit to said processing chamber, whereas operation of said pump with said changeover valve means in said second operative condition enables transfer of reagent from said processing chamber through said fluid conduit to said selected reagent container, and in each said operative condition without providing communication between the atmosphere external to said closed circuit and any one of said pump, said processing chamber or said reagent containers.

14. The tissue processing apparatus of claim 13, wherein said accumulator comprises a compliant bag.

15. A tissue processing apparatus, comprising:

a processing chamber for processing a tissue specimen;

a plurality of reagent containers;

a selector valve interconnected with said reagent containers and with said processing chamber for creating a fluid conduit between a selected reagent container and said processing chamber;

a pump having a suction port and a pressure port and adaptable to provide both a vacuum and a compressed gas;

changeover valve means interconnected with said pump, with said processing chamber and with said reagent containers, said changeover valve means having first and second selectable operative conditions, said first selectable operative condition connecting said suction port of said pump with said processing chamber and said pressure port of said pump with said reagent containers, and said second selectable operative condition connecting said suction port of said pump with said reagent containers and said pressure port of said pump with said processing chamber, thereby in each said operative condition to establish a closed circuit comprising said pump, said processing chamber, said fluid conduit and said selected reagent container;

a pressure relief valve means for relieving excess pressure in said closed circuit;

whereby operation of said pump with said changeover valve means in said first operative condition enables transfer of reagent from said selected reagent container through said fluid conduit to said processing chamber, whereas operation of said pump with said changeover valve means in said second operative condition enables transfer of reagent from said processing chamber through said fluid conduit to said selected reagent container, and in each said operative condition without providing communication between the atmosphere external to said closed circuit and any one of said pump, said processing chamber or said reagent containers.

16. The tissue processing apparatus of claim 15, in which said pressure relief valve means relieves both under-pressure and over-pressure in said closed circuit.

17. The tissue processing apparatus of claim 15, in which said pressure relief valve means comprises a pair of pressure relief valves, one connected to relieve over-pressure and the other connected to relieve under-pressure.

18. The tissue processing apparatus of claim 15, further comprising a filter associated with said pressure relief valve means to filter gas passing said valve means.

* * * * *